United States Patent [19]

Fujii et al.

[11] Patent Number: 4,620,005
[45] Date of Patent: Oct. 28, 1986

[54] 1-ISOPROPYL-4[(4-TETRAHYDRO-1-NAPHTHOYLOXY PHENYL)(ALKYLENE)-CARBONYL(OXYMETHLCARBONYL)]PIPERAZINES HAVING CHYMOTRYPSIN-INHIBITORY ACTIVITY

[75] Inventors: Setsuro Fujii, Toyonaka; Eizou Hattori, Sakado; Mitsuteru Hirata, Saitama; Hisashi Kunieda, Higashi-Murayama; Koichiro Watanabe, Niiza; Hiroshi Ishihama, Higashi-Murayama, all of Japan

[73] Assignee: Kowa Co., Ltd., Nagoya, Japan

[21] Appl. No.: 787,714

[22] Filed: Oct. 17, 1985

Related U.S. Application Data

[63] Continuation of Ser. No. 613,058, May 22, 1984, abandoned.

[30] Foreign Application Priority Data

Jun. 2, 1983 [JP] Japan ................... 58-98713

[51] Int. Cl.[4] .................. C07D 241/04; A61K 31/495
[52] U.S. Cl. .................... 544/391; 544/398; 544/399; 544/400; 544/402
[58] Field of Search ............... 544/383, 386, 390, 391, 544/399, 400, 402, 398

[56] References Cited

U.S. PATENT DOCUMENTS 3,846,430 11/1974 de Antoni et al. ............ 544/393
4,443,603 4/1984 Fujii et al. .................... 544/400

FOREIGN PATENT DOCUMENTS 67561 12/1982 European Pat. Off. ........... 544/386
71433 2/1983 European Pat. Off. .
158737 12/1981 Japan .
38243 3/1983 Japan .

OTHER PUBLICATIONS

Kohjin Co., Ltd., Chem. Abst., 99-38809c.
Kowa Co., Ltd., Chem. Abst., 96-180955d.

Primary Examiner—Donald G. Daus
Assistant Examiner—Cecilia Shen
Attorney, Agent, or Firm—Oblon, Fisher, Spivak, McClelland & Maier

[57] ABSTRACT

Phenyl tetrahydronaphthylcarboxylate of the formula:

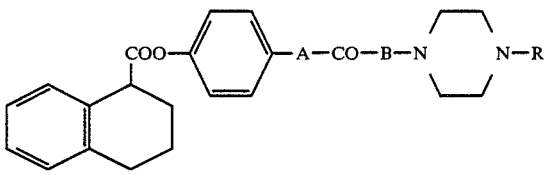

wherein A is a direct bond, or a lower alkylene, vinylene or imino group; B is a direct bond, a lower alkylene or —NH-lower alkylene group, or an —OCH$_2$CO— residual group; and R is a lower alkyl group, with the proviso that A and B are not direct bonds simultaneously, and A, B and R are not a lower alkylene group, a direct bond and a methyl group, respectively, at the same time, are effectively useful as chymotrypsin inhibitors.

4 Claims, No Drawings

1-ISOPROPYL-4[(4-TETRAHYDRO-1-NAPH-THOYLOXY PHENYL)(ALKYLENE)-CARBONYL(OXYMETH-LCARBONYL)]PIPERAZINES HAVING CHYMOTRYPSIN-INHIBITORY ACTIVITY

This application is a continuation of application Ser. No. 613,058, filed May 22, 1984 now abandoned.

BACKGROUND OF THE INVENTION

1. Field of the Invention

This invention relates to novel phenyl tetrahydronaphthylcarboxylate derivatives, and more specifically to such a phenyl tetrahydronaphthylcarboxylate derivative represented by the following formula (I):

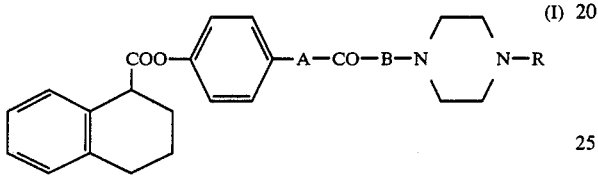

wherein A is a direct bond, or a lower alkylene, vinylene or imino group; B is a direct bond, a lower alkylene or —NH-lower alkylene group, or an —OCH$_2$CO— residual group; and R is a lower alkyl group, with the proviso that A and B are not direct bonds simultaneously, and A, B and R are not a lower alkylene group, a direct bond and a methyl group, respectively, at the same time.

2. Prior Art

Numerous phenyl esters have been previously found by the present inventors which can exert remarkable chymotrypsin inhibitory effects (Japanese Patent Laid-open Publication No. 38243/1983).

The present inventors have further synthesized a series of compounds analogous to such phenyl esters and have determined their physiological activities. Through these research efforts leading to this invention, it has been discovered that phenyl tetrahydronapthylcarboxylates of the formula (I) above and their acid addition salts have more excellent inhibitory effects on chymotrypsin.

SUMMARY OF THE INVENTION

This invention provides compounds of the formula (I) and their acid addition salts.

These compounds are useful by virtue of their chymotrypsin inhibitory characteristics for various purposes, for example, as drugs for the therapy of pancreatic diseases.

DETAILED DESCRIPTION

Compounds of the formula (I) according to this invention can be prepared, for example, by esterifying tetrahydronaphthylcarboxylic acids of the formula (II) below with 4-substituted phenols of the formula (III) below in accordance with the following reaction scheme:

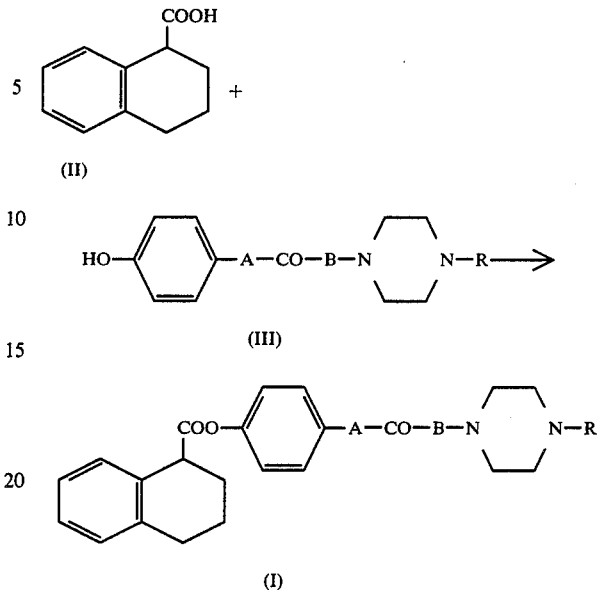

wherein all the symbols have the same meanings as defined above.

The esterification reaction noted above may be carried out by methods commonly employed in the art. One suitable method useful in the invention is to react reactive derivatives of the compounds of the formula (II), such as their acid halides, acid anhydrides, mixed acid anhydrides, active esters, azides and the like with the compounds of the formula (III). Another advantageous method involves reacting the compounds of the formula (II) with the compounds of the formula (III) in the presence of a dehydrating agent such as dicyclohexylcarbodiimide or the like.

Where it is found desirable, the thus obtained compounds of the formula (I) may be converted in conventional manner to inorganic or organic acid addition salts thereof. Eligible inorganic acids include for example hydrochloric acid, sulfuric acid, phosphoric acid, hydrobromic acid and like acids. Eligible organic acids include for example acetic acid, propionic acid, maleic acid, fumaric acid, tartaric acid, oxalic acid, citric acid, methanesulfonic acid, benezenesulfonic acid, toleunesulfonic acid and like acids.

Some selected compounds of this invention were tested with respect to their chymotrypsin inhibitory effects.

The tests were conducted in accordance with the procedure of Muramatsu et al [The Journal of Biochemistry, 62, 408 (1967)]. A mixture was prepared which was made up of 0.1 ml of a dimethylsulfoxide solution of each test compound, 0.1 ml of water and 0.1 ml of a buffer solution containing 10 μg/ml of chymotrypsin (0.1M Tris-HCl buffer, pH 8.0). The mixture was incubated for 10 minutes, followed by addition of 0.2 ml of a buffer solution containing 25 mM of an ethyl ester of acetyl-L-tyrosine. The resulting mixture was reacted at 37° C. for 30 minutes. The remaining substrate was caused to develop a color by the Hesterin method, whereupon its absorbance was measured at 530 nm. As a comparative compound, use was made of tosylphenylalanine chloromethyl ketone (TPCK) which is known as an inhibitor for chymotrypsin.

The results are shown in Table 1 in which the numbers of the test compounds are indicated as those of the corresponding examples given hereunder.

| Test Compound | Inhibitory Activity [50% Inhibitory Concentration (M)] |
|---|---|
| 1 | $4 \times 10^{-6}$ |
| 2 | $3 \times 10^{-6}$ |
| 3 | $7 \times 10^{-7}$ |
| 4 | $6 \times 10^{-7}$ |
| 5 | $3 \times 10^{-8}$ |
| Comparative compound (TPCK) | $5 \times 10^{-4}$ |

This invention will now be described by way of the following examples.

EXAMPLE 1

1-Isopropyl-4-[{4-(1,2,3,4-tetrahydro-1-naphthoyloxy)-phenyl}carbamoylmethyl]piperazine.dihydrochloride (1) One hundred milliliters of an ethanol solution containing 7 g of 1-isopropylpiperazine, 6.2 g of ethyl chloroacetate and 9.2 m of triethylamine was heated and refluxed for 4 hours. After being concentrated under reduced pressure, the resulting mixture was added with ethyl acetate. Insoluble matter was removed by filtration. Thereafter, the residue was purified by silica gel chromatography (eluent: a 20:1 mixture of chloroform and methanol) to obtain 7.4 g of 1-ethoxycarbonylmethyl-4-isopropylpiperazine as a light brownish oily substance.

The oily substance thus obtained was dissolved in a solution consisting of 75 ml of ethanol and 3.5 ml of water, followed by addition of 1.6 g of sodium hydroxied. The mixture was stirred overnight and then neutralized with hydrochloric acid. Insoluble matter was removed by filtration and concentrated under reduced pressure. The resulting oily substance was dissolved in chloroform. The chloroform solution was dried, whereupon the solvent was removed by distillation to obtain 4.76 g of 1-hydroxycarbonylmethyl-4-issopropylpiperazine as light brownish powder.

To 6 ml of a chloroform solution containing 559 mg of the thus obtained compound, 109 mg of p-aminophenol and 36 mg of 4-dimethylaminopyridine was added 619 mg of dicyclohexylcarbodiimide. The reaction mixture was stirred at room temperature for 2 hours. After being concentrated under reduced pressure, the resulting mixture was added with 10 ml of ethyl acetate. Insoluble matter was removed by filtration, and the residue was extracted with 10 ml of 1N HCl. After being neutralized with sodium hydrogencarbonate, the mixture was extracted with 20 ml of chloroform. The chloroform layer was washed with an aqueous saturated NaCl solution and dried, and the solvent was removed by distillation to obtain 410 mg of a light yellowish substance. Thereafter, the substance was dissolved in 3 ml of methanol, followed by addition of 1.5 ml of an aqueous ammonia solution. The resulting mixture was stirred overnight and then concentrated under reduced pressure to obtain 255 mg of 1-(4-hydroxyphenyl)carbamoylmethyl-1-isopropylpiperazine as a yellowish substance.

(2) To 10 ml of an ethyl acetate solution containing 684 mg of the 1-(4-hydroxyphenyl)carbamoylmethyl-4-isopropylpiperazine obtained in item 1) above, 650 mg of 1,2,3,4-tetrahydro-1-naphthylcarboxylic acid and 45 mg of dimethylaminopyridine was added 770 mg of dicyclohexylcarbodiimide. The reaction mixture was stirred at room temperature for 2 hours. Insoluble matter was removed by filtration. The residue was extracted with 10 ml of 1-N HCl and then neutralized with sodium hydrogencarbonate. After being washed with water and dried, the resulting mixture was concentrated under reduced pressure to obtain a light yellowish substance. The substance was purified by silica gel column chromatography (eluent: a 20:1 mixture of chloroform and methanol) and dissolved in 20 ml of ethanol. To the ethanol solution was added hydrochloric acid to obtain 684 mg (yield: 54.6%) of 1-isopropyl-4-[{4-(1,2,3,4-tetrahydro-1-naphthoyloxy)phenyl}carbamoylmethyl]-piperazine dihydrochloride as colorless crystals having a melting point of 235° to 240° C. (decomposed).

EXAMPLES 2 to 7

The procedures of Example 1 were repeated to obtain six compounds of the formula (I), details of which are tabulated in Table 2.

TABLE 2

| Example No. | Compound (I) A | B | R | Salt | Yield (%) | Appearance | Melting Point (°C.) |
|---|---|---|---|---|---|---|---|
| 2 | —CH=CH— | — | —CH(CH₃)₂ | HCl | 61.5 | Colorless crystals | 207–210 |
| 3 | — | —NHCH₂CH₂— | —CH(CH₃)₂ | — | 38.1 | Light yellowish crystals | 102–103 |
| 4 | —CH=CH— | — | —CH₃ | (COOH)₂ | 72.2 | Colorless powdery crystals | 146–150 |
| 5 | — | —OCH₂CO— | —CH(CH₃)₂ | HCl | 56.8 | Colorless crystals | 196.5–198 |
| 6 | —CH₂CH₂— | — | —CH(CH₃)₂ | HCl | 35.8 | Colorless needle-like crystals | 169–171 |

TABLE 2-continued

| Example No. | Compound (I) A | B | R | Salt | Yield (%) | Appearance | Melting Point (°C.) |
|---|---|---|---|---|---|---|---|
| 7 | —CH$_2$— | — | —CH(CH$_3$)CH$_3$ | HCl | 56.3 | Colorless needle-like crystals | 188–192 |

What is claimed is:

1. A phenyl tetrahydronaphthylcarboxylate having the formula:

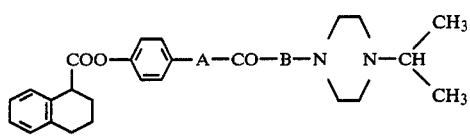

wherein A is a direct bond, or a lower alkylene group and B is a direct bond, or a —OCH$_2$CO— group, with the proviso that A and B are not direct bonds simultaneously.

2. The compound, 1-isopropyl-4-[(4-(1,2,3,4-tetrahydro-1-naphthoyloxy)phenyl)carbonyloxymethyl carbonyl]piperazine.

3. The compound, 1-isopropyl-4-[(4-(1,2,3,4-tetrahydro-1-naphthoyloxy)phenyl)ethyl carbonyl]piperazine.

4. The compound, 1-isopropyl-4-[(4-(1,2,3,4-tetrahydro-1-naphthoyloxy)phenyl)methylcarbonyl]piperazine.

* * * * *